US005621012A

United States Patent [19]

Schönrock et al.

[11] Patent Number: 5,621,012
[45] Date of Patent: Apr. 15, 1997

[54] ACTIVE COMPOUND COMBINATIONS HAVING A CONTENT OF GLYCERYL ALKYL ETHERS AND COSMETIC AND DERMATOLOGICAL FORMULATIONS COMPRISING SUCH ACTIVE COMPOUND COMBINATIONS

[75] Inventors: Uwe Schönrock, Norderstedt; Joachim Degwert, Tostedt; Friedhelm Steckel, Hamburg, all of Germany

[73] Assignee: Beiersdorf Aktiengesellschaft, Hamburg, Germany

[21] Appl. No.: 457,770

[22] Filed: Jun. 1, 1995

[30] Foreign Application Priority Data

Jun. 14, 1994 [DE] Germany .......................... 44 20 625.9

[51] Int. Cl.⁶ ............................ A61K 31/16; A61K 7/42; A61K 31/08

[52] U.S. Cl. ........................ 514/629; 514/723; 514/729; 424/59

[58] Field of Search .................. 424/59; 514/629, 514/723, 729

[56] References Cited

U.S. PATENT DOCUMENTS 4,847,071  7/1989  Bissett et al. ............................ 424/59

*Primary Examiner*—Shelley A. Dodson
*Attorney, Agent, or Firm*—Sprung Horn Kramer & Woods

[57] ABSTRACT

Active compound combinations comprising active contents of (a) one or more glycerol ethers of saturated and/or unsaturated, branched and/or unbranched aliphatic alcohols having 12 to 24 carbon atoms, (b) bisabolol and/or panthenol (c) and if appropriate one or more substances chosen from the group consisting of cosmetically or dermatologically acceptable antioxidants.

9 Claims, No Drawings

ACTIVE COMPOUND COMBINATIONS HAVING A CONTENT OF GLYCERYL ALKYL ETHERS AND COSMETIC AND DERMATOLOGICAL FORMULATIONS COMPRISING SUCH ACTIVE COMPOUND COMBINATIONS

The present invention relates to active compounds and formulations comprising such active compounds for cosmetic and dermatological treatment and/or prophylaxis of erythematous, inflammatory, allergic or autoimmune-reactive symptoms, in particular dermatoses. The invention furthermore relates to the use of such active compounds and formulations comprising such active compounds for immunostimulation of the skin, and advantageously here also for immunostimulation in the context of treatment of damaged skin, in particular for treatment of wounds.

The invention furthermore relates to formulations having an extremely low so-called "stinging potential".

The skin, especially the epidermis, as a barrier organ of the human organism, is subject to external actions to a particular degree. According to current scientific understanding, the skin represents an immunological organ which, as an immunocompetent peripheral compartment, plays its own role in inductive, effective and regulative immune processes of the total organism.

The epidermis is richly equipped with nerves and nerve end apparatuses, such as Vater-Pacini lamellated bodies, Merkel cell neuritis complexes and free nerve endings for pain, cold and heat sensation and itching.

Immunosuppression in general is suppression or weakening of the reactivity of the immune system. Immunosuppression can be divided into local and systemic effects. In the end, it comprises a large number of widely varying aspects, all of which include reduction of the normal immunological defence mechanisms of the skin.

In humans with sensitive, susceptible or vulnerable skin, a neurosensory phenomenon called "stinging" (sting=traumatize, burn, hurt) can be observed. This "sensitive skin" differs in principle from "dry skin" with thickened and hardened horny layers.

Typical reactions of "stinging" on sensitive skin are reddening, tightening and burning of the skin and itching.

Itching of atopic skin and itching with skin diseases are to be regarded as neurosensory phenomena.

"Stinging" phenomena can be regarded as disturbances to be treated cosmetically. Severe itching, on the other hand, especially severe itching of the skin which occurs with atopy, can also be described as a more serious dermatological disturbance.

Typical troublesome neurosensory phenomena associated with the terms "stinging" or "sensitive skin" are reddening of the skin, tingling, prickling, tightening and burning of the skin and itching. They can be caused by stimulating environmental conditions, for example massage, action of surfactants, the influence of weather, such as sun, cold, dryness, and also damp heat, radiant heat and UV radiation, for example from the sun.

In "Journal of the Society of Cosmetic Chemists" 28, pages 197–209 (May 1977), P. J. Frosch and A. M. Kligman describe a method for estimating the "stinging potential" of topically administered substances. Lactic acid and pyruvic acid, for example, are employed as positive substances here. During measurement by this method, however, amino acids, in particular glycine, have also been determined as substances having a neurosensory action (such substances are called "stingers").

According to knowledge to date, such a sensitivity towards quite specific substances occurs differently in individuals. This means that a person who experiences "stinging effects" on contact with a substance will with a high probability experience it repeatedly on any further contact. However, contact with other "stingers" can just as easily proceed without any reaction.

Many more or less sensitive persons also suffer erythematous skin symptoms on using some deodorant or antiperspirant formulations.

Erythematous skin symptoms also occur as concomitant symptoms with certain skin diseases or irregularities. The typical skin eruption with the clinical picture of acne, for example, is regularly reddened to a greater or lesser degree.

The object of the present invention was thus to remedy the disadvantages of the prior art.

In particular, active compounds and formulations comprising such active compounds for cosmetic and dermatological treatment and/or prophylaxis of erythematous, inflammatory, allergic or autoimmune-reactive symptoms, in particular dermatoses, and also the clinical picture of "stinging" were to be provided.

Such active compounds and formulations comprising such active compounds which can be used for immunostimulation of the skin, and here advantageously also for immunostimulation in the context of an action promoting wound healing, were furthermore to be provided.

Astonishingly, active compound combinations comprising active contents (a) of one or more glycerol ethers of saturated and/or unsaturated, branched and/or unbranched aliphatic alcohols having 12 to 24 carbon atoms, (b) bisabolol and/or panthenol (c) and if appropriate one or more substances chosen from the group consisting of cosmetically or dermatologically acceptable antioxidants, remedy the disadvantages of the prior art.

The present invention in particular relates to the use of active compound combinations comprising active contents of (a) one or more glycerol ethers of saturated and/or unsaturated, branched and/or unbranched aliphatic alcohols having 12 to 24 carbon atoms, (b) bisabolol and/or panthenol (c) and if appropriate one or more substances chosen from the group consisting of cosmetically or dermatologically acceptable antioxidants, for treatment and/or prophylaxis of erythematous skin symptoms and/or for stimulation of the immune system, in particular for wound healing.

The substance combinations according to the invention act synergistically in respect of the particular individual substances. In this context they display an antiphlogistic, antierythematous, immunostimulating and wound healing-promoting action.

The use of the present active compound combinations or formulations for prophylaxis or treatment of erythematous skin symptoms or for healing wounds is advantageous, and in particular also the use of such active compound combinations for the preparation of formulations for prophylaxis or treatment of erythematous skin symptoms or for healing wounds.

The substance combinations according to the invention can be used either in cosmetic or in medicinal formulations.

The use of the individual substances in cosmetics and dermatic agents is indeed widely known. U.S. Pat. No.

3,294,639 thus describes a method for treatment of inflammatory symptoms using an active amount of batyl alcohol, chimyl alcohol and/or selachyl alcohol.

The antiinflammatory action or other physiological action of such glyceryl ethers can, moreover, be seen from scientific publications: R. G. Burford, C. W. Gowdey, Arch. Int. Pharmacodyn., 1968, 173, No. 1, page 56 et seq.; J. Bodman, J. H. Maisin, "The α-Glyceryl Ethers", Clinica Chimica Acta Volume 3, 1958, page 253 et seq.

In contrast, the active compound combinations according to the invention and the advantageous properties thereof cannot be deduced from the prior art.

According to the invention, the glycerol ethers are preferably distinguished by the following structure:

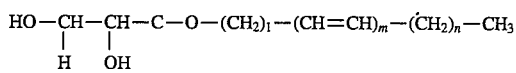

In this formula, the indices l, m and n assume values from 0 to 23, with the proviso that the sum of l+n+(2×m) must give numbers in the range between 11 and 23.

Advantageous representatives of the glycerol esters according to the invention are, for example, chimyl alcohol

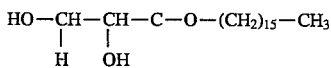

(α-hexadecyl glyceryl ether),
selachyl alcohol

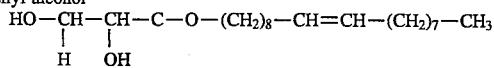

(α-9-octadecenyl glyceryl ether)
and, especially preferably,
batyl alcohol

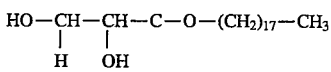

(α-octadecyl glyceryl ether).

α-Bisabolol, chemically: [(−)-6-methyl-2-(4-methyl-3-cyclohexenyl)-5-hepten-2-ol], is a substance which occurs in camomile oil and has an antiphlogistic and spasmolytic action. It is used both in the field of cosmetics (for example as a perfume fixative) and in medicine. It is characterized by the structural formula

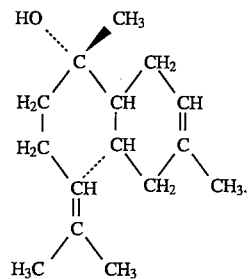

Panthenol, chemically: 2,4-dihydroxy-N-(3-hydroxypropyl)-3,3-dimethylbutyramide, is known to be employed in the field of cosmetics, and also for the treatment of inflammations. It is characterized by the structural formula

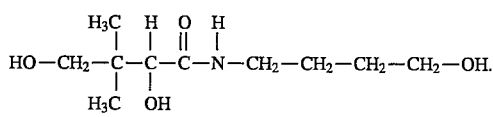

All the antioxidants suitable or customary for cosmetic and/or dermatological uses can be used according to the invention as antioxidants which are favourable but nevertheless optionally to be used.

The antioxidants are particularly advantageously chosen from the group consisting of ascorbic acid (vitamin C), ascorbic acid derivatives, the various tocopherols (vitamin E) and tocopheryl esters and other tocopherol derivatives, folic acid (formerly called vitamin $B_c$, $B_9$ or M, now assigned to the vitamin $B_2$ group), phytic acid (inositol-hexaphosphoric acid, also fytic acid), the various ubiquinones (mitoquinones, coenzyme Q), bile extract, cis- and/or transurocanic acid (4-imidazolylacrylic acid), carnosine (N-β-alanyl-L-histidine, ignotine), histidine, flavones or flavonoids, cystine (3,3'-dithiobis(2-aminopropionic acid)), cysteine (2-amino-3-mercaptopropionic acid) and derivatives thereof (for example N-acetylcysteine), the various carotenes (in particular β-carotene and lycopene (psi-carotene)), tyrosine (2-amino-3-(4-hydroxyphenyl)propionic acid), α-liponic acid (1,2-dithiolane-3-pentanoic acid), glutathione (gamma-L-glutamyl-L-cysteineglycine) and glutathione esters.

It is advantageous to choose the ratio of glycerol alkyl ethers to bisabolol and/or panthenol from the range from 1:20 to 20:1, preferably 1:5 to 5:1, in particular 2:3 to 3:2.

If two or more glycerol alkyl ethers are present, or if bisabolol and panthenol are employed at the same time, the ratio of the total amount of glycerol alkyl ethers to the total amount of bisabolol and panthenol is advantageously chosen from the range from 1:20 to 20:1, preferably 1:5 to 5:1, in particular 2:3 to 3:2.

It is furthermore advantageous to choose the ratio of glycerol alkyl ethers to bisabolol and/or panthenol to antioxidants from the range from 1:1:20 to 20:20:1, preferably 1:1:5 to 5:5:1.

If two or more glycerol alkyl ethers or antioxidants are present, or if bisabolol and panthenol are employed at the same time, the ratio of the total amount of glycerol alkyl ethers to the total amount of bisabolol and panthenol to the total amount of antioxidants is advantageously chosen from the range from 1:1:20 to 20:20:1, preferably 1:1:5 to 5:5:1.

In cosmetic or dermatological formulations, the individual concentrations of the active compound combinations according to the invention are preferably 0.01–10% by weight of one or more glycerol ethers of saturated and/or unsaturated, branched and/or unbranched aliphatic alcohols having 12 to 24 carbon atoms, 0.5–5% by weight of bisabolol and/or panthenol and 0.1–2.5% by weight of one or more substances chosen from the group consisting of cosmetically or dermatologically acceptable antioxidants, in each case based on the total weight of the cosmetic or dermatological formulations.

If bile extract and/or α-liponic acid are used as antioxidants according to the invention, it is advantageous to choose the particular concentrations thereof from the range from 0.001–2% by weight, based on the total weight of the formulation.

If vitamin E and/or derivatives thereof are used as antioxidants according to the invention, it is advantageous to choose the particular concentrations thereof from the range from 0.001–4% by weight, based on the total weight of the formulation.

If retinoids, carotenes and/or derivatives thereof and/or lycopene are used as antioxidants according to the invention, it is advantageous to choose the particular concentrations thereof from the range from 0.001–10% by weight, based on the total weight of the formulation.

If urocanic acid is used as the antioxidant according to the invention, it is advantageous to choose its concentration from the range from 0.001–2.00% by weight, based on the total weight of the formulation.

It is of course known to the expert that high-quality cosmetic compositions are usually inconceivable without the customary auxiliaries and additives. These include, for example, agents which impart consistency, fillers, perfume, colouring agents, emulsifiers, additional active compounds, such as vitamins or proteins, light protection agents, stabilizers, insect repellents, alcohol, water, salts, antimicrobially, proteolytically or keratolytically active substances and the like.

Mutatis mutandis, corresponding requirements apply to the formulation of medical formulations.

Topical medical compositions as a rule comprise one or more medicaments in an active concentration. For simplicity, for a clear distinction between cosmetic and medical use and corresponding products, reference is made to the legal provisions of the Federal Republic of Germany (for example cosmetics legislation, Food and Drugs Act).

It is likewise advantageous to add the active compound combinations according to the invention, as an additive, to formulations which already comprise other active compounds for other purposes.

The compositions according to the invention can accordingly be used, for example, depending on their build-up, as a skin protection cream, cleansing milk, sun screen lotion, nutrient cream, day or night cream and the like. Where appropriate, it is possible and advantageous to use the compositions according to the invention as a base for pharmaceutical formulations.

In particular, the active compound combinations according to the invention can be used as an additive in cosmetic deodorants or antiperspirants. The customary substances known to the expert can then be used as agents having a deodorant or antiperspirant action. For example, the formation of perspiration may be suppressed by astringents—chiefly aluminium salts, such as aluminium hydroxychloride (aluminium chlorohydrate).

The bacterial flora on the skin may be reduced by the use of antimicrobial substances in cosmetic deodorants. In the ideal case, only the microorganisms causing odour should be effectively reduced. Monocarboxylic acid esters of di- and triglycerol, for example, are advantageous. However, other antimicrobially active substances are also suitable.

According to the invention, the use of active compounds which are in themselves not especially mild is even possible and, where appropriate, advantageous since the possible erythema-promoting action thereof can be compensated by the active compound combinations according to the invention.

The use of the active compound combinations in skincare cosmetic and/or dermatological formulations is also regarded as an advantageous embodiment of the present invention.

For use, the cosmetic and dermatological formulations according to the invention are applied to the skin in an adequate amount in the manner customary for cosmetics.

Those cosmetic and dermatological formulations which are in the form of a sunscreen agent are also favourable. These preferably comprise, in addition to the active compound combinations according to the invention, additionally at least one UVA filter substance and/or at least one UVB filter substance and/or at least one inorganic pigment.

However, it is also advantageous, in the context of the present invention, to compile those cosmetic and dermatological formulations of which the main purpose is not protection from sunlight, but which nevertheless comprise a content of UV protection substances. Thus, for example, UVA and UVB filter substances are usually incorporated into day creams.

Formulations according to the invention furthermore can advantageously comprise substances which absorb UV radiation in the UVB range, the total amount of the filter substances being, for example, 0.1% by weight to 30% by weight, preferably 0.5 to 10% by weight, in particular 1 to 6% by weight, based on the total weight of the formulations, in order to provide cosmetic and/or dermatological formulations which protect the skin from the entire range of ultraviolet radiation. They can also be used as sunscreen agents.

The UVB filters can be oil-soluble or water-soluble. Oil-soluble substances which are to be mentioned are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate;

2,4,6-trianilino-(p-carbo-2'-ethyl-1'-hexyloxy)-1,3,5-triazine.

Water-soluble substances which may be mentioned are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)sulphonic acid and their salts.

The list of UVB filters mentioned which can be used in combination with the active compound combinations according to the invention is of course not intended to be limiting.

The invention also relates to the combination of a UVA filter according to the invention with a UVB filter, and to a cosmetic or dermatological formulation according to the invention which also comprises a UVB filter.

It may also be advantageous to combine the active compound combinations according to the invention with UVA filters which cosmetic and/or dermatological formulations usually comprise. Such substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations or formulations which comprise these combinations. The same amounts of UVA filter substances which have been mentioned for UVB filter substances can be used.

Cosmetic and/or dermatological formulations comprising the active compound combinations according to the invention can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. They are particularly preferably pigments based on titanium dioxide. The amounts mentioned for the above combinations can be used.

Cosmetic and dermatological formulations according to the invention for protection of the skin from UV rays can be in various forms, such as are usually employed, for example, for this type of formulation. They can thus be, for example, a solution, an emulsion of the water-in-oil (W/O) type or of the oil-in-water (O/W) type, or a multiple emulsion, for example of the water-in-oil-in-water (W/O/W) type, a gel, a solid stick or else an aerosol.

Emulsions according to the invention, for example in the form of a skin protection cream, a skin lotion or a cosmetic milk, for example in the form of a sunscreen cream or a sunscreen milk, are advantageous and comprise, for example, the fats, oils, waxes and other fatty substances mentioned, as well as water and an emulsifier such as is usually used for such a type of formulation.

It is also possible and advantageous in the context of the present invention to introduce the active compound combinations according to the invention into aqueous systems or surfactant formulations for cleansing of the skin and hair.

The cosmetic and dermatological formulations according to the invention can comprise cosmetic auxiliaries such as are usually used in such formulations, for example preservatives, bactericides, perfumes, substances for preventing foaming, colouring agents, pigments which have a colouring action, thickeners, surface-active substances, emulsifiers, softening, moistening and/or humectant substances, fats, oils, waxes or other customary constituents of a cosmetic or dermatological formulation, such as alcohols, polyols, polymers, foam stabilizers, electrolytes, organic solvents or silicone derivatives.

If the cosmetic or dermatological formulation is a solution or emulsion, solvents which can be used are:

water or aqueous solutions;

oils, such as triglycerides of capric or caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids; and alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water may be a further constituent.

Gels according to the invention usually comprise alcohols of low C number, for example ethanol, isopropanol, 1,2-propanediol and glycerol, and water or an abovementioned oil in the presence of a thickening agent, which, in oily-alcoholic gels, is preferably silicon dioxide or an aluminium silicate, and in aqueous-alcoholic or alcoholic gels is preferably a polyacrylate.

Solid sticks according to the invention comprise, for example, naturally occurring or synthetic waxes, fatty alcohols or fatty acid esters. Lip care sticks are preferred.

Suitable propellants for cosmetic and/or dermatological formulations according to the invention which can be sprayed from aerosol containers are the customary known readily volatile, liquefied propellants, for example hydrocarbons (propane, butane or isobutane), which can be employed by themselves or in a mixture with one another. Compressed air can also advantageously be used.

The expert of course knows that there are propellent gases which are in themselves non-toxic and would in principle be suitable for the present invention, but which should nevertheless be omitted because of an unacceptable action on the environment or other concomitant circumstances, in particular fluorohydrocarbons and fluorochlorohydrocarbons (CFCs).

Cosmetic and dermatological formulations according to the invention for use on the hair are, for example, shampooing agents, formulations which are used when rinsing the hair before or after shampooing, before or after permanent wave treatment or before or after colouring or bleaching the hair, formulations for blow-drying or setting the hair, formulations for colouring or bleaching, a styling or treatment lotion, a hair lacquer or a permanent wave agent.

If appropriate, the cosmetic and/or dermatological formulations comprise additional active compounds, auxiliaries and/or additives such as are usually used for this type of formulation for hair care and hair treatment. Auxiliaries which are used are preservatives, surface-active substances, substances for preventing foaming, emulsifiers, thickening agents, fats, oils, waxes, organic solvents, bactericides, perfumes, colouring agents or pigments, the task of which is to colour the hair or the cosmetic or dermatological formulation itself, electrolytes and additional substances for regreasing the hair or the scalp.

Cosmetic formulations which are a skin cleansing agent or shampooing agent preferably comprise at least one anionic, nonionic or amphoteric surface-active substance, or else mixtures of such substances, an active amount of active compound combinations according to the invention, and auxiliaries such as are usually used for this purpose. The surface-active substance or the mixtures of these substances can be present in the shampooing agent in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, the formulations are, for example, aqueous or aqueous-alcoholic solutions which, if appropriate, comprise surface-active substances, preferably nonionic or cationic surface-active substances, the concentration of which can be between 0.1 and 10% by weight, preferably between 0.2 and 5% by weight. These cosmetic and/or dermatological formulations can also be aerosols with the auxiliaries usually used for this purpose.

A cosmetic formulation in the form of a lotion which is not rinsed out, in particular a lotion for setting the hair, a lotion which is used while blow-drying the hair or a styling and treatment lotion, is in general an aqueous, alcoholic or aqueous-alcoholic solution and comprises at least one cationic, anionic, nonionic or amphoteric polymer or mixtures thereof, as well as the active compound combinations according to the invention. The amount of polymers used is, for example, between 0.1 and 10% by weight, preferably between 0.1 and 3% by weight.

Cosmetic formulations according to the invention for treatment and care of the hair which comprise active compound combinations according to the invention can be in the form of emulsions which are of the nonionic or anionic type. Nonionic emulsions comprise, in addition to water, oils or fatty alcohols, which can also be polyethoxylated or polypropoxylated, for example, or else mixtures of the two organic components. If appropriate, these emulsions comprise cationic surface-active substances.

Cosmetic formulations for treatment and care of the hair can be in the form of gels which, in addition to an active content of the active compound combinations according to the invention and solvents usually used for this purpose, preferably water, also comprise organic thickening agents, for example gum arabic, xanthan gum, sodium alginate, cellulose derivatives, preferably methylcellulose, hydroxymethylcellulose, hydroxyethylcellulose, hydroxypropylcellulose and hydroxypropylmethylcellulose, or inorganic thickening agents, for example aluminium silicates, such as, for example, bentonites, or a mixture of polyethylene glycol and polyethylene glycol stearate or distearate. The gel comprises the thickening agent, for example, in an amount of between 0.1 and 30% by weight, preferably between 0.5 and 15% by weight.

The cosmetic and dermatological formulations according to the invention can comprise cosmetic auxiliaries such as are usually used in such formulations, for example preservatives, bactericides, perfumes, substances for preventing foaming, colouring agents, pigments which have a colouring action, thickening agents, surface-active substances, emulsifiers, softening, moistening and/or humectant substances, fats, oils, waxes or other conventional constituents of a cosmetic or dermatological formulation, such as alcohols, polyols, polymers, foam stabilizers, electrolytes, organic solvents or silicone derivatives.

The following examples are intended to illustrate the present invention.

EXAMPLE 1

| Ointment, W/0 emulsion | % by weight |
|---|---|
| (a) | |
| Microcrystalline wax + pentaerythrityl-cocoate + stearyl citrate + gliceryloleate + aluminium stearate + propylene glycol (Dehymuls F, Henkel) | 8.00 |
| Decyl oleate (Cetiol V, Henkel) | 7.00 |
| Petrolatum (Vaseline BD, Witco) | 20.00 |
| Paraffin oil | 12.00 |
| Microcrystalline wax | 2.00 |
| (b) | |
| Olive oil | 12.00 |
| Batyl alcohol | 2.50 |
| (c) | |
| Panthenol (Roche) | 2.50 |
| Preservative | q.s. |
| Perfume | q.s. |

-continued

| Ointment, W/0 emulsion | % by weight |
|---|---|
| (d) | |
| Glycerol | 3.00 |
| MgSO$_4$ | 0.70 |
| Water | to 100.00 |

Preparation: phases (a), (b) and (d) are heated separately to 75° C. Phases (a) and (b) are then stirred uniformly into phase (d). Thereafter, the mixture is cooled to about 65° C., homogenized and then cooled to about 40° C. The panthenol and if desired suitable amounts of preservatives and/or perfume are introduced into the resulting mixture in succession. The mixture is then cooled to 30° C. and homogenized once again.

EXAMPLE 2

| Cream, O/W emulsion | % by weight |
|---|---|
| (a) | |
| Glyceryl stearate SE (Tegin Normal, Th. Goldschmidt) | 1.00 |
| Ceteareth 20 (Eumulgin B2, Henkel) | 1.00 |
| Petrolatum (Vaseline BD, Witco) | 1.00 |
| Paraffin oil | 14.00 |
| Cetearyl alcohol (Lanette O, Henkel) | 1.50 |
| (b) | |
| Propylene glycol | 5.00 |
| Batyl alcohol | 2.50 |
| (c) | |
| D-panthenol 75 L (Roche) | 2.50 |
| Carbomer (Synthalen M, Sigma Chemie) | 0.80 |
| Water | 20.00 |
| Preservative | q.s. |
| (d) | |
| Perfume | q.s. |
| (e) | |
| NaOH (45% strength) | 0.60 |
| Water | to 100.00 |

Preparation: phases (a), (b) and (e) are heated separately to 75° C. Phases (a) and (b) are then stirred uniformly into phase (e). Thereafter, the mixture is cooled to about 65° C., homogenized and then cooled to about 40° C. Phases (c) and (d) and if desired a suitable amount of perfume are introduced into the resulting mixture in succession. The mixture is then cooled to 30° C. and homogenized once again.

EXAMPLE 3

| Lotion, W/O emulsion | % by weight |
|---|---|
| (a) | |
| Paraffin oil | 9.50 |
| Aluminium stearate | 0.35 |
| (b) | |
| PEG 40 sorbitan peroleate (Arlatone T, Henkel) | 2.00 |
| Polyglycerol 3-diisostearate (Lameform TGI, Henkel) | 2.00 |
| Petrolatum (Vaseline BD, Witco) | 1.70 |
| Cetyl palmitate (Cutina CP, Henkel) | 1.50 |

| Lotion, W/O emulsion | % by weight |
|---|---|
| (c) | |
| Isohexadecane (Solvent IH) | 6.00 |
| (d) | |
| Propylene glycol | 5.00 |
| Batyl alcohol | 2.50 |
| (e) | |
| D-panthenol 75 L (Roche) | 2.50 |
| Preservative | q.s. |
| Perfume | q.s. |
| (f) | |
| MgSO$_4$ | 0.60 |
| Water | to 100.00 |

Preparation: phase (a) is heated to 120° C. and then cooled to 80° C. Phases (b) and (d) are heated separately to 80° C. Phases (b) and (d) are then stirred uniformly into phase (a). The combined phases (a), (b) and (d) are added to phase (f), which has been heated to 75° C., and thereafter the mixture is cooled to 65° C. and homogenized. Phase (c) is added and the mixture is cooled to 40° C. The constituents (e) are stirred in, and the mixture is cooled to 30° C. and homogenized again.

EXAMPLE 4

| Lotion, O/W emulsion | % by weight |
|---|---|
| (a) | |
| Acrylate/C$_{10-30}$-alkyl acrylate copolymer (Pemulen TR 1, Goodrich) | 0.30 |
| Cetearyl alcohol (Lanette O, Henkel) | 2.00 |
| C$_{12-15}$Alkyl benzoates (Finsolv TN, Erblöh) | 3.00 |
| (b) | |
| D-panthenol 75 L (Roche) | 2.50 |
| (c) | |
| Ethanol | 5.00 |
| Batyl alcohol | 2.50 |
| (d) | |
| Preservative | q.s. |
| Perfume | q.s. |
| (e) | |
| Butane-1,3-diol | 10.00 |
| NaOH (45% strength) | 0.22 |
| Water | to 100.00 |

Preparation: phases (a) and (e) are heated to 75° C. and then cooled to 65° C. The combined phases are homogenized and cooled to 40° C. Panthenol, phase (c) and if appropriate the constituents (d) are stirred into the mixture in succession. The mixture is cooled to 30° C. and homogenized again.

EXAMPLE 5

| Gel | % by weight |
|---|---|
| (a) | |
| Propylene 1,2-glycol | 5.00 |
| Batyl alcohol | 2.50 |
| (b) | |
| Bisabolol | 2.50 |

| Gel | % by weight |
|---|---|
| (c) | |
| Carbomer (Carbopol 2984) | 0.80 |
| (d) | |
| NaOH (45% strength) | 0.70 |
| (e) | |
| Preservative | q.s. |
| Perfume | q.s. |
| (f) | |
| PEG-150 (Polywachs 6000S, Hüls) | 4.00 |
| Sorbitol | 0.50 |
| Water | to 100.00 |

Preparation: phases (a) and (f) are heated separately to 75° C. and stirred together. The bisabolol is stirred uniformly into the combined phases, the carbomer is then stirred in and the mixture is cooled to 65° C. and homogenized. After neutralizing with NaOH, the mixture is cooled to 40° C. The constituents (e) are added, if desired, and the mixture is then homogenized again.

EXAMPLE 6

| Ointment, W/O emulsion | % by weight |
|---|---|
| (a) | |
| Microcrystalline wax + pentaerythrityl cocoate + stearyl citrate + glyceryl oleate + aluminium stearate + propylene glycol (Dehymuls F, Henkel) | 8.00 |
| Decyl oleate (Cetiol V, Henkel) | 7.00 |
| Petrolatum (Vaseline BD, Witco) | 20.00 |
| Paraffin oil | 12.00 |
| Microcrystalline wax | 2.00 |
| α-Tocopheryl acetate | 0.50 |
| (b) | |
| Olive oil | 12.00 |
| Batyl alcohol | 2.50 |
| (c) | |
| Panthenol (Roche) | 2.50 |
| Preservative | q.s. |
| Perfume | q.s. |
| (d) | |
| Glycerol | 3.00 |
| MgSO$_4$ | 0.70 |
| Water | to 100.00 |

Preparation: phases (a), (b) and (d) are heated separately to 75° C. Phases (a) and (b) are then stirred uniformly into phase (d). Thereafter, the mixture is cooled to about 65° C., homogenized and then cooled to about 40° C. The panthenol and if desired suitable amounts of preservatives and/or perfume are introduced into the resulting mixture in succession. The mixture is then cooled to 30° C. and homogenized once again.

EXAMPLE 7

| Cream, O/W emulsion | % by weight |
|---|---|
| (a) | |
| Glyceryl stearate SE (Tegin Normal, Th. Goldschmidt) | 1.00 |
| Ceteareth 20 (Eumulgin B2, Henkel) | 1.00 |
| Petrolatum (Vaseline BD, Witco) | 1.00 |
| Paraffin oil | 14.00 |
| Cetearyl alcohol (Lanette O, Henkel) | 1.50 |
| α-Tocopheryl acetate | 0.50 |
| (b) | |
| Propylene glycol | 5.00 |
| Batyl alcohol | 2.50 |
| (c) | |
| D-panthenol 75 L (Roche) | 2.50 |
| Carbomer (Synthalen M, Sigma Chemie) | 0.80 |
| Water | 20.00 |
| Preservative | q.s. |
| (d) | |
| Perfume | q.s. |
| (e) | |
| NaOH (45% strength) | 0.60 |
| Water | to 100.00 |

Preparation: phases (a), (b) and (e) are heated separately to 75° C. Phases (a) and (b) are then stirred uniformly into phase (e). Thereafter, the mixture is cooled to about 65° C., homogenized and then cooled to about 40° C. Phases (c) and (d) and if desired a suitable amount of perfume are introduced into the resulting mixture in succession. The mixture is then cooled to 30° C. and homogenized once again.

EXAMPLE 8

| Lotion, W/0 emulsion | % by weight |
|---|---|
| (a) | |
| Paraffin oil | 9.50 |
| Aluminium stearate | 0.35 |
| (b) | |
| PEG 40 sorbitan peroleate (Arlatone T, Henkel) | 2.00 |
| Polyglycerol 3-diisostearate (Lameform TGI, Henkel) | 2.00 |
| Petrolatum (Vaseline BD, Witco) | 1.70 |
| Cetyl palmitate (Cutina CP, Henkel) | 1.50 |
| α-Tocopheryl acetate | 0.50 |
| (c) | |
| Isohexadecane (Solvent IH) | 6.00 |
| (d) | |
| Propylene glycol | 5.00 |
| Batyl alcohol | 2.50 |
| (e) | |
| D-panthenol 75 L (Roche) | 2.50 |
| Preservative | q.s. |
| Perfume | q.s. |
| (f) | |
| MgSO₄ | 0.60 |
| Water | to 100.00 |

Preparation: phase (a) is heated to 120° C. and then cooled to 80° C. Phases (b) and (d) are heated separately to 80° C. Phases (b) and (d) are then stirred uniformly into phase (a). The combined phases (a), (b) and (d) are added to phase (f), which has been heated to 75° C., and thereafter the mixture is cooled to 65° C. and homogenized. Phase (c) is added and the mixture is cooled to 40° C. The constituents (e) are stirred in, and the mixture is cooled to 30° C. and homogenized again.

EXAMPLE 9

| Lotion, O/W emulsion | % by weight |
|---|---|
| (a) | |
| Acrylate/C₁₀₋₃₀-alkyl acrylate copolymer (Pemulen TR 1, Goodrich) | 0.30 |
| Cetearyl alcohol (Lanette O, Henkel) | 2.00 |
| C₁₂₋₁₅Alkyl benzoates (Finsolv TN, Erbslöh) | 3.00 |
| α-Tocopheryl acetate | 0.50 |
| (b) | |
| D-panthenol 75 L (Roche) | 2.50 |
| (c) | |
| Ethanol | 5.00 |
| Batyl alcohol | 2.50 |
| (d) | |
| Preservative | q.s. |
| Perfume | q.s. |
| (e) | |
| Butane-1,3-diol | 10.00 |
| NaOH (45% strength) | 0.22 |
| Water | to 100.00 |

Preparation: phases (a) and (e) are heated to 75° C. and then cooled to 65° C. The combined phases are homogenized and cooled to 40° C. Panthenol, phase (c) and if appropriate the constituents (d) are stirred into the mixture in succession. The mixture is cooled to 30° C. and homogenized again.

EXAMPLE 10

| Gel | % by weight |
|---|---|
| (a) | |
| Propylene 1,2-glycol | 5.00 |
| Batyl alcohol | 2.50 |
| α-Tocopheryl acetate | 0.50 |
| (b) | |
| Bisabolol | 2.50 |
| (c) | |
| Carbomer (Carbopol 2984) | 0.80 |
| (d) | |
| NaOH (45% strength) | 0.70 |
| (e) | |
| Preservative | q.s. |
| Perfume | q.s. |
| (f) | |
| PEG-150 (Polywachs 6000S, Hüls) | 4.00 |
| Sorbitol | 0.50 |
| Water | to 100.00 |

Preparation: phases (a) and (f) are heated separately to 75° C. and stirred together. The bisabolol is stirred uniformly into the combined phases, the carbomer is then stirred in and the mixture is cooled to 65° C. and homogenized. After neutralizing with NaOH, the mixture is cooled to 40° C. The constituents (e) are added, if desired, and the mixture is then homogenized again.

EXAMPLE 11

| Deodorant cream, O/W emulsion | % by weight |
|---|---|
| (a) | |
| Bisabolol | 2.50 |
| Microcrystalline wax + pentaerythrityl cocoate + stearyl citrate + glyceryl oleate + aluminium stearate + propylene glycol (Dehymuls F, Henkel) | 6.00 |
| Decyl oleate (Cetiol V, Henkel) | 7.00 |
| Octyldodecanol (Eutanol G, Henkel) | 5.00 |
| Petrolatum (Vaseline BD, Witco) | 5.00 |
| (b) | |
| Batyl alcohol | 2.50 |
| Ethanol | 5.00 |
| (c) | |
| Preservative | q.s. |
| Perfume | q.s. |
| (d) | |
| Aluminium chlorohydrate (Locron P, Hoechst) | 20.00 |
| Water | to 100.00 |

Preparation: phases (a) and (b) are heated separately to 75° C. and added to phase (d), which has likewise been heated to 75° C., and the mixture is cooled to 65° C. After homogenizing, the mixture is cooled to 40° C. The constituents (c) are added if desired, and thereafter the mixture is cooled to 30° C. and homogenized again.

EXAMPLE 12

| Deodorant cream, O/W emulsion | % by weight |
|---|---|
| (a) | |
| Bisabolol | 2.50 |
| Microcrystalline wax + pentaerythrityl cocoate + stearyl citrate + glyceryl oleate + aluminium stearate + propylene glycol (Dehymuls F, Henkel) | 6.00 |
| Decyl oleate (Cetiol V, Henkel) | 7.00 |
| Octyldodecanol (Eutanol G, Henkel) | 5.00 |
| Petrolatum (Vaseline BD, Witco) | 5.00 |
| α-Tocopheryl acetate | 0.50 |
| (b) | |
| Batyl alcohol | 2.50 |
| Ethanol | 5.00 |
| (c) | |
| Preservative | q.s. |
| Perfume | q.s. |
| (d) | |
| Aluminium chlorohydrate (Locron P, Hoechst) | 20.00 |
| Water | to 100.00 |

Preparation: phases (a) and (b) are heated separately to 75° C. and added to phase (d), which has likewise been heated to 75° C., and the mixture is cooled to 65° C. After homogenizing, the mixture is cooled to 40° C. The constituents (c) are added if desired, and thereafter the mixture is cooled to 30° C. and homogenized again.

We claim:

1. Active compound combinations comprising active contents of
   (a) one or more glycerol ethers of saturated and/or unsaturated, branched and/or unbranched aliphatic alcohols having 12 to 24 carbon atoms,
   (b) bisabolol and/or panthenol,
   (c) and optionally one or more substances chosen from the group consisting of cosmetically or dermatologically acceptable antioxidants, wherein the ratio of the total amount of (a) to the total amount of (b) ranges from 1:20 to 20:1.

2. Active compound combinations according to claim 1, wherein the glycerol ethers have the structure

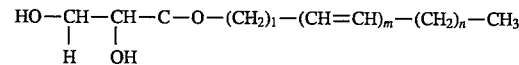

wherein the indices l, m and n assume values from 0 to 23, with the proviso that the sum of $l+n+(2\times m)$ must give numbers in the range between 11 and 23.

3. Active compound combinations according to claim 2, wherein the glycerol ethers are chosen from the group consisting of chimyl alcohol, selachyl alcohol and batyl alcohol.

4. Active compound combinations according to claim 1, wherein the ratio of the total amount of glycerol alkyl ethers (a) to the total amount of bisabolol and panthenol (b) being in the range from 1:5 to 5:1.

5. Active compound combinations according to claim 1, wherein the ratio of the total amount of glycerol alkyl ethers to the total amount of bisabolol and panthenol to the total amount of antioxidants is chosen from the range from 1:1:20 to 20:20:1.

6. Cosmetic or dermatological formulations having a content of active compound combinations according to claim 1.

7. Formulations according to claim 6, which comprise
   0.01–10% by weight of one or more glycerol ethers of saturated and/or unsaturated, branched and/or unbranched aliphatic alcohols having 12 to 24 carbon atoms,
   0.5–5% by weight of bisabolol and/or panthenol and
   0.1–2.5% by weight of one or more substances chosen from the group consisting of cosmetically or dermatologically acceptable antioxidants.

8. A method of treatment of erythematous skin symptoms or for healing a wound which comprises applying to such skin or wound an amount effective therefor of a combination according to claim 1.

9. A method of treatment of erythematous skin symptoms or for healing a wound which comprises applying to such skin or wound an amount effect therefor of a cosmetic or dermatological formulation according to claim 6.

* * * * *